United States Patent
Kubo

[11] Patent Number: 5,728,288
[45] Date of Patent: Mar. 17, 1998

[54] APPARATUS AND METHOD FOR PRODUCING AIR CONTAINING MINUS ALKALI ION

[75] Inventor: Tetsujiro Kubo, Tokyo, Japan

[73] Assignee: Yugenkaisha Kubo Technical Office, Tokyo, Japan

[21] Appl. No.: 520,789

[22] Filed: Aug. 30, 1995

[51] Int. Cl.$^6$ .................................................. C02F 1/461
[52] U.S. Cl. ..................... 205/763; 205/764; 205/745; 204/248; 204/249; 204/277; 204/278
[58] Field of Search ........................... 205/745, 763, 205/764; 204/248, 249, 277, 278

[56] References Cited

U.S. PATENT DOCUMENTS

| | | | |
|---|---|---|---|
| 4,493,637 | 1/1985 | Ganter et al. | 431/190 |
| 5,108,618 | 4/1992 | Hirasawa | 210/689 |
| 5,211,689 | 5/1993 | Kobayashi | 206/0.5 |

Primary Examiner—Arun S. Phasge
Attorney, Agent, or Firm—Wenderoth, Lind & Ponack

[57] ABSTRACT

Production of air containing minus alkali ion. As shown in FIG. 2, there is shown an electric stone fine powder 20 having the grain size of 0.3 to 3 microns on the average, an electric stone carrier having the electric stone fine powder 20 uniformly mixed therewith, which is in the form of clothes having a volume intrinsic DC electric resistance of $10^7$ to $10^{10}$ $\Omega$.cm. This constitutes a vent contact reaction portion 2 as shown in FIG. 3. This portion 2 is located above an air intake 1a at the lower part of a box 1 and extended over the whole internal surface of the box 1. Ventilation means 3 formed from an electric fan causes the electric stone carrier 30 to subject to direct forced ventilation into contact with air, and minus alkali ion is prepared from water molecules which are moisture in air. The air containing the minus alkali ion is delivered from an air port 1b provided at the upper part of the box 1 to an installation spot.

8 Claims, 3 Drawing Sheets

APPARATUS AND METHOD FOR PRODUCING AIR CONTAINING MINUS ALKALI ION

BACKGROUND OF THE INVENTION

1. Field of the Invention

The present invention is directed to an apparatus and method for producing air containing minus alkali ions. More specifically, The present invention is concerned with a method for modifying air in a living environment, an apparatus for the modification, and an apparatus and method in which minus alkali ions (hydroxyl ions) contained in the modified air are absorbed on the surface of a body and into the body by respiration to bring forth a useful effect in the health and medical fields.

Accordingly, the present apparatus can be used to modify air within rooms of hospitals, old-age homes, homes, working places and others. The air prepared by the method for producing air containing minus alkali ions brings forth a remarkable deodorizing effect, and is utilized in combination with other health and medical practices.

2. Description of the Related Art

Experts in their respective fields have studied on a large scale for more than 50 years the subject of ions contained in the air having various functions. Accordingly, the method and apparatus for producing useful minus ions have been studied. However, since the definition and idea of ions are wrong, the studies on the production method and apparatus came to a deadlock. Since the point of the present invention resides in such a definition, this will be mentioned in detail hereinafter.

First, an "Air ion" and "Air ion producing unit" will be described. It is well known that the health of the human race is greatly affected by the condition of the air. From the early twentieth century, fine particles with a charge present in the air have been discovered in various countries, which leads to the birth of the idea of and term "air ions". A number of studies have been carried out in the fields of physics, meteorology, health-physiology and therapeutics for practical application.

In the past, an air ion generator makes use of a discharge in air between electrodes, which includes the following depending on the shapes of the electrodes.

(1) The tip - flat plate
(2) Filament - flat plate
(3) Filament - cylinder
(4) Filament - net-like flat plate (cylinder)

A power supply comprises a primary side of AC 100 V and a secondary high voltage side of a neotransformer or the like, in which air is ionized by discharge using a high voltage of 3,000 V or more. Positive and negative ions generated are allowed to pass through an electric filter to take out either of the positive and negative ion substances.

Despite the fact that the studies on the minus air ions in many effective medical fields have been reported, a minus air ion generator has not yet been put to practical use for a half century. The reason why is that conventionally, air which is an electric insulator is ionized by discharge using a high voltage of 3,000 V or more. Depending on such a high voltage discharge, ozone ($O_3$), nitrogen oxide (NO), $NO_2$ and some other active oxygen molecules, other than minus ions are generated, and these are difficult to be removed merely by separating them by an electric filter.

It is known that the substances such as ozone are harmful to the human body. Recently, it is known that lipid peroxide and active oxygen lead to aging and cancer. Further, the electric filter for removing a harmful plus air ion is not satisfactory in terms of its construction, effect and efficiency. Accordingly, air ion has been greatly expected and researched for a long time of period, but at present is not successful for practical use.

Recently, a device whose principle and construction are almost the same as an air ion generator is marketed under the name of "an ion type air cleaner". This is a system not using a fan in which ion air generated between electrodes is utilized to adhere fumes of a cigarette or the like to a filtration sheet of paper. Still, a note on the generation of ozone is mentioned in a manual for these goods. This construction remains the same as the old type which uses the filament-flat plate or filament-cylindrical discharge electrode.

Despite the unfinished technical stage, the study on the so-called "air ions" in the medical field has been long made in the world. Particularly, many studies in physiology and therapeutics are widely announced in many literatures and books including clinical experiments. This indicates to have a great meaning and value enough to employ again by the present new scientific technique, as an unsolved and important theme even at present after a half century. The medical studies on the air ion made by many laboratory workers in many countries from old have a great meaning that gives a motive to the study of this invention by the patent applicant of the present invention.

Typical examples of books relating to the air ion include the following. These books include a detailed description in connection with the medical and physiological effects of "air ion".

I. Theory and practice of Air Ion, by Shoichi Kimura, Doctor of Medicine, and Masahiro Taniguchi, Doctor of Medicine, published by Nankaido, May 8, 1938.

This book comprises 226 pages in total, including 309 internal and external literatures, which has general control over internal and external studies relating to air ion. This book was prepared by the united efforts of government and people in Hokkaido University, Osaka University and others under the assistance of the Japan Academy, the Japan Association for the promotion of Science and the like.

In this book, the "air ion" is classified as follows:

1. Free electrons
2. Atomic ions (positive and negative)
3. Light ions (positive and negative)
4. Heavy ions Positive or negative light ions or electrons are adhered to fine particles such as dust, mist, fume and the like.

5. Intermediate ions

Intermediate size between the light ions and heavy ions. Only two kinds of light ions and heavy ions are ordinary present in the atmosphere near the surface of the earth. Also, in the following book, items 4 to 10, [Ion Generator] (page 504 to 508), an air ion and an air ion generator are summarized.

II. Electrostatic Handbook, published by Chijin Shoten Edited by High Polymer Society, January 1967—First Edition October 1991—Re-edition The above two books have been published quite differently in that their dates of publication are considerably apart from each other, but the definition and idea of "air ion" and "ion" mentioned therein remain almost the same. That is, the "ion" and many kinds of charged fine "particles" are confused. The method for producing air ion and apparatus thereof are based on the wrong idea of the air ion. This way of thinking about the air ion is based on the then knowledge of physics, which may be unavoidable but is an unsatisfactory or inadequate knowledge in consideration of the present state of affairs.

First, the difference between the definition of "air ion" and the concept thereof generally used today will be described.

(1) Definition of "ion"

According to Physics and Chemistry Dictionary (4th edition) (Jun. 10, 1993), page 63: an "ion" is "an atom having a charge or an atomic group (including molecules)". Further, at present, this physics and chemistry dictionary uses no phrase of "air ion".

(2) On the other hand, according to "Electrostatic Handbook" (Oct. 11, 1993 edited by High Polymer Society), issued by editing internal and external literatures up to the present in the physical and medical fields on the "air ion", in the description of "air ion" appearing on pages 504 to 508 in respect of "Ion Generator" in items 4 to 10 thereof, there is described "Ions are present in the atmosphere, the ions being classified into small ions, medium ions, intermediate ions and large ions according to the sizes thereof", in which also, the old definition of "ion" is used.

From 1930 or so, the charged fine particles which are present in air are called "air ions", which physical and meteorological studies start, and in 50 years ago, the medical and physiological studies on the "air ion" with respect to the human body were actively made in various countries in the world. As a result, many studies and reports and books were announced, of which studies were however discontinued with the occurrence of the second world war. Today, those studies have not been succeeded by new studies.

In the second half of the 20th century, the remarkable high growth of industry results in an increase of factories, a thick population growth, an increase of automobiles, a rapid increase of energy utilization, formation of cities, and the like, thereby leading to material contaminations of the atmosphere resulting in an increase of new diseases. Simultaneously, the general environmental contamination including that of water now poses a great global problem. The present invention has as its problem to solve the absence of a method and apparatus not only for purifying the present contaminated air but for modifying air to be useful for improving health of human being and treatment and prevention of diseases.

There gives rise to a meaning that again studies the scientific definition of the aforementioned conventional "air ion". The patent applicant of the present invention has searched and studied in detail these many past results, and as a result reached the following conclusion.

1. The conventional definition and idea of "air ions" are totally different from "ions" used in the present physics. New study and development and work should be constituted on the basis of proper definition and idea.

2. The aforementioned basic error leads to a deadlock of the studies of a measurement method of "air ions" and a method and apparatus for the production thereof, and new studies should be made returning to the fundamentals.

3. On the other hand, it is reported in the medical and physiological fields that the air ion is classified according to the size of particles thereof, and among large, medium and small ions, a light ion (also called "minus air ion") having a minus charge of the small ion gives good operation and effect for the human body. It is further reported by many laboratory workers that an air ion having a plus charge give unfavorable operation and effect. However, an air ion is produced by a high voltage discharge in air using a neotransformer on the basis of a short-circuit idea in which air is merely ionized to prepare air ion. This method naturally generates minus ions and plus ions and various kinds of compounds. Under the high voltage discharge of thousands of volts, many dangerous $O_1^-$, $O_2^-$, $O_3^-$, $NO^-$, and $NO_2$ compounds are generated also in the minus ion.

What on the earth is "minus ion" which gives the action effective for the human body? The ion substance required is not yet specified. In this connection, a light ion having a minus charge is merely expressed. Further, it is not understood whether such a substance is single, or a mixture of several minus ions. Under such an indefinite knowledge on the air ion, it is impossible to prepare a generator or a measurement unit thereof. Further, it is not understood what on the earth is prepared or what is measured.

However, on the other hand, in consideration that the study on the medical and medical effects is made for the human body, it is not considered that the scientific and clinical diagnoses and evaluation of medical science and physiology will be the extremely different conclusion with respect to the effect of applying the air ion to the human body between the 50 years ago and the present. The indefiniteness of the substance of the air ion applied to the human body gives rise to all the problems.

Being the study under these circumstances, with respect to the relationship between the so-called "air ion" and the human body in terms of medical treatment and physiology, the following conclusion is obtained by many laboratory workers in various countries. These phenomenon and fact are reliable. "Generally, the effect of the minus air ion is calmative which is effective for pain relieving, hypnotism, cough relieving, sweat suppression, appetite promotion, blood pressure drop, refreshing, fatigue prevention and the like, whereas the plus air ion has actions, conversely to the former, such as stimulation, insomnia, headache, unpleasantness, increase in blood pressure, high temperature feeling, and the like." Such a physiological action of the "air ion" is greatly attracted by many countries. The artificial production of air ion for the environments health within buildings, contamination of the atmosphere, city health, and health management in the industrial society poses an important problem for study. However, this great problem has not yet been put into any shape because the substance of the air ion is indefinite.

SUMMARY OF THE INVENTION

The apparatus and method for producing air containing minus alkali ion according to the present invention is intended to ionize water in air instead of ionization of air itself, in view of the technical problem noted above. That is, the inventor of the present application has paid attention to the presence of water in air. The water in air is called moisture, quantity of which is expressed by humidity. The water is a small assembly in which water molecules are 2 or 3 and which floats in air. The radius of a water molecule is $1.5 \times 10^8$ cm.

The detailed configuration of the apparatus and method for producing air containing minus alkali ions according to the present invention will be described in detail hereinafter. First, the configuration of the apparatus for producing air containing minus alkali ions described in claim 1 of the present invention will be described. First, there is present an electric stone fine powder. This electric stone fine powder has the grain size of 0.3 to 3microns on the average. Next, there is present an electric stone carrier. The aforesaid electric stone fine powder is uniformly mixed with the electric stone carrier, whose volume intrinsic DC electric resistance is $10^7$ to $10^{10}\Omega.\text{cm}$, and which has a large air contact area such as cloth-like, honeycomb-like or grain-like configuration. There is further present ventilation means. By this ventilation means, the electric stone carrier is subjected to direct forced ventilation to contact with air.

Next, the configuration of the apparatus for producing air containing minus alkali ion of the invention described in claim 2 of the apparatus and method for producing air containing minus alkali ion according to the present invention will be described. This invention has the same configuration as that of the invention of claim 1 described above except the following. Therefore, the whole sentence of the description of the configuration of the invention described in claim 1 as described above is herein quoted, to which is added the description of the following configuration. The difference from the configuration of the invention of claim 1 resides in the presence of water which comes in contact with the electric stone carrier by way of immersion. This water comes in contact with a part or the whole of the electric stone carrier, in which a part or the whole thereof is immersed into a water-containing vessel, and the surface of water is subjected to forced ventilation by ventilation means into contact with air whereby vaporization is effected from the surface of water to provide moisture of air.

Alternatively, the electric stone carrier itself may comprise a vessel. Water is injected into the vessel, and the vessel is subjected to forced ventilation through the surface of water to provide contact.

Then, the configuration of the method for producing air containing minus alkali ion of the invention described in claim 3 of the apparatus and method for producing air containing minus alkali ion according to the present invention will be described. First, electric stone fine powder having the grain size of 0.2 to 3 microns on the average are uniformly mixed, whose volume intrinsic DC electric resistance is $10^7$ to $10^0\Omega.\text{cm}$, the electric stone carrier having a large air contact area such as cloth-like, honeycomb-like or grain-like configuration is subjected to direct forced ventilation by ventilation means to provide contact, and water (moisture) in air is ionized to prepare a minus ion.

Next, the configuration of the method for producing air containing minus alkali ion of the invention described in claim 4 of the apparatus and method for producing air containing minus alkali ion according to the present invention will be described. This invention has the same configuration as that of the invention of claim 3 described above except the following. Therefore, the whole sentence of the description of the configuration of the invention described in claim 3 as described above is herein quoted, to which is added the description of the following configuration. The difference from the configuration of the invention of claim 3 resides in the presence of water which comes in contact with the electric stone carrier. This water comes in contact with a part or the whole of the electric stone carrier, in which a part or the whole thereof is immersed into a water-containing vessel, and the surface of water is subjected to forced ventilation by ventilation means into contact with air.

Alternatively, the electric stone carrier itself may comprise a vessel. Water is injected into the vessel, and the vessel is subjected to forced ventilation through the surface of water to provide contact.

preferably, the electric stone carrier described in claims 1, 2, 3 or 4 described above may comprise a fibrous or rubber elastic material (elastomer) or ceramic.

The apparatus and method for producing air containing minus alkali ion according to the present invention overthrows the conventional academic theory, and therefore, the fundamental theory of the operation thereof will be first mentioned. First, the function of hydroxyl ion $H_3O_2^-$ ($H_2.OH^-$) will be described.

(1) Absorption from the surface of the body and the respiratory organs

When the hydroxyl ion acts on the body through the lungs, it tends to permeate into the cell walls of endothelial cells of the lung. The ion causes the cell permeation force to enhance as proved by the reports of Mr. Matsuoka and Mr. Yuwamoto mentioned above. Thereby, the hydroxyl ion moves into blood through the cells of blood capillaries together with electrons carried by the ion. The blood carries the minus ion carried with electrons to the tissues of the whole body to adjust the acid strength of blood to a weak alkalinity (pH 7.5). The ion having a gentle surfactant action is to form cholesterol into colloid and disperse it to relieve coagulation of blood. As a result, blood pressure is lowered to quicken the circulation of the blood, improving the metabolism, growth and internal secretion function.

The surfactant action of the ion causes the hydration of cells in the body to enhance (enhancement of affinity with water) to strengthen the resistance against the disease. The ion enters also from the surface of the body other than the lung to exhibit the effect similar to that by aspiration, as can be seen from the experiments by Mr. Ashiba.

See Blood pressure dropping action of air ion and its quantitative relationship, by Masanobu Ashiba; Ikai-Jihoh, January 1937

The air (minus air ion) containing hydroxyl ion (minus alkali ion) prepared by the present invention is prepared by ionization of water molecules which are moisture components by intermittent discharge by way of permanent electrodes of an electric stone which is a natural substance. By the fact that substances other than the water molecules are not contained and the gentle surfactant action of the hydroxyl ion, even if the concentration thereof increases within the liquid, pH value has the nature being saturated and does not exceed 7.0 to 7.5. This has been made sure in ordinary water, and no danger or injury is given to the human body from a viewpoint of the process of production. Rather, the minus air ion pursued by many laboratory workers in many countries over the past half century has a minus charge and comprises a hydration coupling of OH ion and water molecules which are the index of a degree of alkali, which is preferable for humor of the body. Further, the gentle surfactant action exhibited by the hydroxyl ion exerts the positive action on the human body such as the movement of the ion substance into the body, the prevention of coagulation or adhesion of cholesterol, and the purification of wall surfaces of many blood vessels for transporting humor.

Most of the excellent effects exhibited by the then minus air ion in the past many medical and physiological studies and reports can be replaced without modification by the air containing the hydroxyl ion. The absence of harmful minus ion and ozone gas can expect better effects than those called the minus air ion in the past. The study in this field in the future can be expected by the study of experts in the field of medical science and physiology.

Being configurated, the apparatus and method for producing air containing minus alkali ion according to the present invention have the specific functions as follows. First, the function of the apparatus for producing air containing minus alkali ion of the invention described in claim 1 according to the present invention will be described. The electric stone fine power is uniformly mixed with the electric stone carrier, whose volume intrinsic DC electric resistance is $10^7$ to $10^{10} \Omega.cm$, and which has a large air contact area such as cloth-like, honeycomb-like or grain-like configuration. By this ventilation means, the electric stone carrier is subjected to direct forced ventilation to contact with air, and therefore the water molecules in air are formed into minus alkali ion.

Next, the function of the apparatus for producing air containing minus alkali ion of the invention described in claim 2 of the apparatus and method for producing air containing minus alkali ion according to the present invention will be described. This invention has the same function as that of the invention of claim 1 described above except the following. Therefore, the whole sentence of the description of the function of the invention described in claim 1 as described above is herein quoted, to which is added the description of the following configuration. The difference from the function of the invention of claim 1 resides in the presence of water which comes in contact with the electric stone carrier by way of immersion. This water comes in contact with a part or the whole of the electric stone carrier, in which a part or the whole thereof is immersed into a water-containing vessel, and the surface of water is subjected to forced ventilation by ventilation means into contact with air. Accordingly, the formation of water into minus alkali ion is further promoted. Further, not only the water is formed into minus alkali ion but also the electric stone carrier is subjected to direct forced ventilation whereby water molecules in air are formed into minus alkali ion.

Alternatively, the electric stone carrier itself may comprise a vessel. Water is injected into the vessel, and the vessel is subjected to forced ventilation through the surface of water to provide contact. In this case, the function can be also obtained.

Then, the function of the method for producing air containing minus alkali ion of the invention described in claim 3 of the apparatus and method for producing air containing minus alkali ion according to the present invention will be described. First, electric stone fine powder having the grain size of 0.2 to 3 microns on the average are uniformly mixed, whose volume intrinsic DC electric resistance is $10^7$ to $10^{10} \Omega.cm$, the electric stone carrier having a large air contact area such as cloth-like, honeycomb-like or grain-like configuration is subjected to direct forced ventilation by ventilation means to provide contact. Therefore, water (moisture) in air is ionized to produce minus ion.

Next, the function of the method for producing air containing minus alkali ion of the invention described in claim 4 of the apparatus and method for producing air containing minus alkali ion according to the present invention will be described. This invention has the same function as that of the invention of claim 3 described above except the following. Therefore, the whole sentence of the description of the function of the invention described in claim 3 as described above is herein quoted, to which is added the description of the following function. The difference from the function of the invention of claim 3 resides in the presence of water which comes in contact with the electric stone carrier. This water comes in contact with a part or the whole of the electric stone carrier, in which a part or the whole thereof is immersed into a water-containing vessel, and the surface of water is subjected to forced ventilation by ventilation means into contact with air. Further, not only the water is formed into minus alkali ion but also the electric stone carrier is subjected to direct forced ventilation whereby water molecules in air are formed into minus alkali ion.

Alternatively, the electric stone carrier itself may comprise a vessel. Water is injected into the vessel, and the vessel is subjected to forced ventilation through the surface of water to provide contact.

EXAMPLES

The invention on which the present application is based will be first described. The patent applicant of the present invention has found in October 1989 that permanent electrodes were present in an electric stone, and then found that when a fine electrode (3 microns on the average) possessed by the fine crystals and ceramic granular substances carrying the former are used to effect feeble electrolysis of decomposition pressure of water (theoretical value: 0.7 V), hydroxyl ion $H_3O_2^-$ and hydrogen gas $H_2$ ($H^+ + e \rightarrow H \rightarrow H_2$) are generated in water so that the hydroxyl ion has properties of the surfactant substance. It is presumed that $H.O^-$ as a hydrophobic group and water molecule.$H_2O$ as a hydrophilic group are bonded, which was announced on the academic magazine [Solid physics] (December 1989, 24. 12). The actual proof of this theory was supplemented by prof. Terutaro Nakamura, the ex-professor of Tokyo University, Prof. Morioka of the Faculty of Agriculture, Kochi University, and Mr. Yuwamoto et al. of Food Dept., the Ministry of Agriculture, Forestry and Fishery, this being now called "Kubo Theory" by these actual proofs.

The applicant of the present invention thought that the phenomenon similar to the feeble electrolysis by way of permanent electrodes of an electric stone in water as a liquid occurs between water molecules as humidity components in air or assemblies (about two or three) of water molecules and the permanent electrodes of the electric stone. Various forms such as the state where one $HO^-$ and water molecule $H_2O$ and the state called hydration in which more than two or three water molecules are gently bonded would be present. However, if the opinion that the humidity component in air is generally an assembly of two or three water molecules is correct, it is considered that one water molecules out of them is ionized and $H^+$ ion is formed into hydrogen gas, and the remaining one $HO^-$ and one or two water molecules are bonded.

Unlike that the hydroxyl ions are in water, they are separated from each other and float in air. The respective hydroxyl-ions are isolated by air. Moreover, since the charges of ion are minus charges, they repel each other, and they are in the dispersed state without coagulation and assembly by Braun motion.

Other than such ions or a combination of ions and molecules or an assembly of molecules, there are present in air, many particles much larger than molecules called charged particles and charged to positive and negative. Many of them are contaminated substances in air such as dust and fume generated from various exhausts not called ions. Conventionally, these are also called air ions. Most of them are charged to plus, and since they are large in size and small in mobility, which tend to be adhered to the surface of solids and can be easily collected by electric precipitation.

In the study in terms of many medical science, treatment, physiology and clinic in many countries in the world when the substance of air ion is almost indefinite 50 years ago, the substance of minus air ion is named minus light ion despite the former is not clarified, and it was quite fumble. The massive report does not lose the important historical meaning even if the minus air ion is specified to be the hydroxyl ion by the patent applicant of the present invention. Instead, the report involves many suggestions and is helpful for development in the future.

DETAILED DESCRIPTION OF PREFERRED EMBODIMENTS

EXPERIMENTAL EXAMPLES

Experimental examples will be described hereinbelow.
Experimental Example I

Content: A "minus air ion generator" is manufactured. The experiment was conducted to confirm the following.

Figure 1:
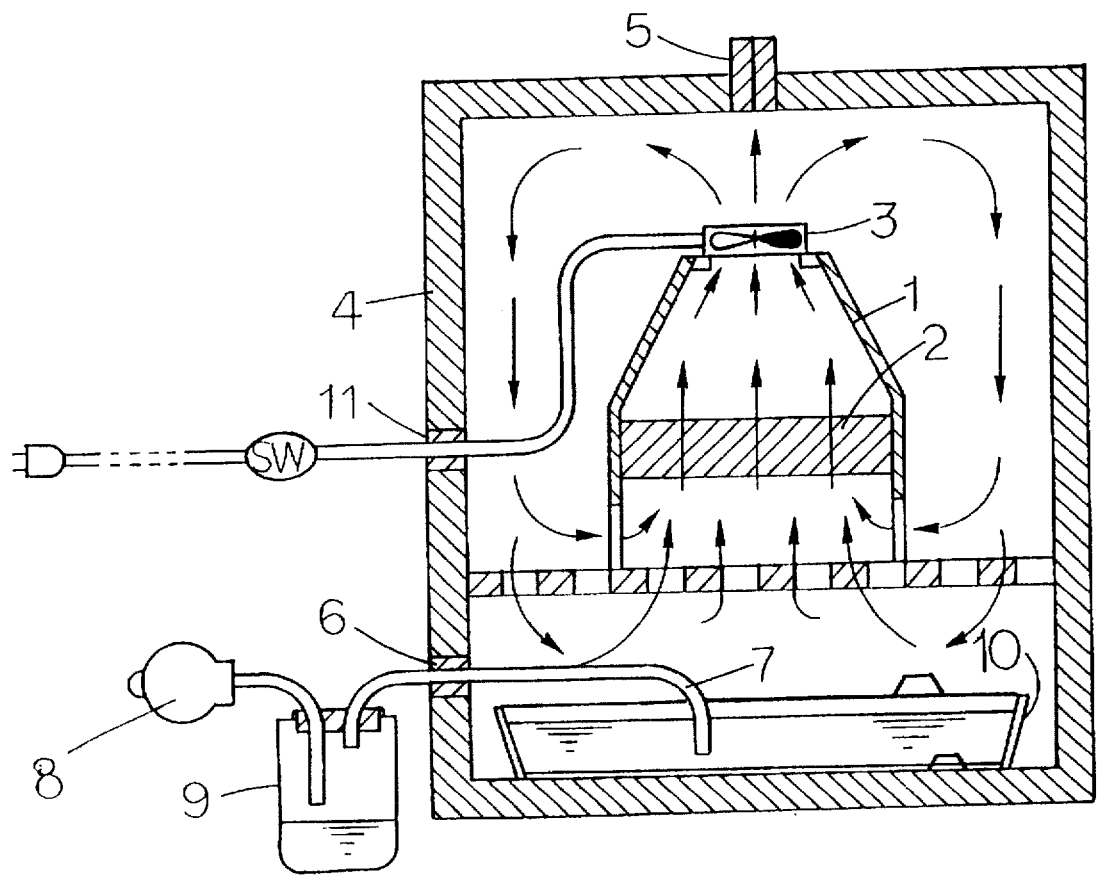
FIG. 1 is a front sectional view of one embodiment of an experimental apparatus for an apparatus for producing air containing minus alkali ion according to the present invention.

Object: To qualitatively actually prove that water molecules as humidity components in air come in contact with rayon fibers carrying crystals having permanent electrodes to generate a discharge reaction whereby hydrogen gas is separated from OH ion. Experimental Apparatus:

This apparatus is shown in FIG. 1. In FIG. 1, reference numeral 1 designates a wooden box, and 2 designates a ventilation contact reaction portion, which is an electric stone carrier formed of non-woven fabric of rayon. Reference numeral 3 designates a ventilation axial-flow fan of 12 VDC, 4 designates a vacuum desiccator of an acryl plate, and 5 designates a sampling collecting opening for gas chromatograph with a packing. Reference numeral 6 designates a teflon tube insert opening for collecting water, 7 designates a teflon tube, and 8 designates a pressure-reduced rubber ball (intake) for collecting water. Reference numeral 9 designates a water storage bottle for intaking sample water, 10 designates a water storage tray, and 11 designates a power source sealing insert opening.

Method:

The vacuum desiccator formed from a thick acryl plate (15 mm thick) is used to put a tray with water therein on a bottom in the closed box. An apparatus having a construction as shown in a separate sheet is put on the shelf (bored with many air holes). Here, this is called a minus ion air generator. Air in the box is always circulated by the axial flow fan located in the central portion of the top plate of the apparatus. This air passes, without fail, through a mat in which rayon non-woven fabrics having a venting property and a large contact area are placed one above another formed of "rayon fibers carrying an electric stone" provided on the bottom surface of the apparatus.

When the assembly of water molecules as moisture components in air comes close to a position several microns (5 to 10μ) from the center of fine crystals (0.3 to 0.4 microns on the average) of he electric stone mixed into the rayon fibers, the water molecules are ionized by the instantaneous discharge, and $H^+$ ion generated by reaction of $H_2O \rightarrow H^+ - OH^-$ is formed into $H_2$ (hydrogen gas), which is scattered into air and $OH^-$ ion is hydrated with $H_2O$ (water molecule) to provide hydroxyl ion $HO^- - H_2O(H_3O_2)$. The $H_3O_{2-}$ hydroxyl ion is a surfactant substance having $HO^-$ as a hydrophobic group and $H_2O$ as a hydrophilic group. $H_3O_2^-$ ion increases in air within the box as the time passes.

When the flow of air which circulates within the box touches the surface of water in the tray on the bottom of the box, the $H_3O_2)$ ion molecules are adsorbed and absorbed into the surface of water. This molecule forms a monomolecular film with the hydrophobic group $H.O^-$ oriented on the surface of water in the direction opposite to the water. This phenomenon is common to all the surfactant substances. As the monomolecular film of the $H_3O_{2-}$ ion covers the surface of water, the bonding force between the water molecules of the surface becomes weakened so that the vaporization is quickened. This increases the (relative) humidity within the closed box.

This action for increasing the humidity results from the monomolecular film formed by the molecules of the surfactant substance on the surface of water, and the amount thereof with respect to the amount of the whole water is very small but the rising value of humidity is large enough to be measured. On the other hand, the generating amount of hydrogen gas corresponds to $HO^-$ ion (or $H_3O_{2-}$ ion), and the amount thereof is difficult even by normal gas chromatography. In presumption, it does not reach 1 ppm (presumed limit) in test time for 2 to 3 days. However, when the fan is stopped for constant time (about 5 minutes) to stop the circulation of air, hydrogen gas is much lighter than air so that the former is concentrated at the top within the box. A sample is collected from air and measured to qualitatively detect the generation of hydrogen gas.

Table 1

Evaluations:

1. The generation of hydrogen gas though extremely fine amount was detected.

(Note) After the fan has been stopped, hydrogen gas moves up to the ceiling of the box and is concentrated to increase its concentration, which was detected by a gas chromatography. Though less than 1 ppm, the peak of hydrogen on the gas chromatograph was observed. (This gas chromatograph is GC-6A manufactured by Shimazu Seisakusho; column : MS-13X 4m×3 mmø, column temperature : 40° C., vaporization room temperature room temperature, detection temperature: 60° C., and detector TCD). 2. The humidity inside the box increases as the time passes, and reaches 51% to 81% after 51 hours. The temperature inside the box remains almost the same. The rise of humidity results from an increase in evaporation speed produced by the generator is adsorbed and absorbed by the contact between the vent and the water surface in the bottom tray.

3. The fact that pH lowers as the time passes and conductivity increases indicates the carbon dioxide gas contained in air within the box is absorbed from the surface of water.

Electric stone carrying rayon fiber used in this experimental example

I (1) Rayon 66.5%

Tourmaline 3.5% (0.4μ on the average)

(2) Polyester 30%

Total 100% (weight ratio)

(3) Coarseness of rayon 7 denier (weight of length 9000 m:7 g (4) Polyester contained cotton, tourmaline contained cotton Non-woven fabric of 75 g/1M2 (called resin cotton)

(5) Electric stone (rough stone)

Made in China (strength electrode strength, C-12)

Powdered to 3μ by Peking Metallurgy Steel Iron Research Institute

After imported, powdered to 0.4 g (average) in Japan

II Vent material for vent contact portion (1) 15 cm×15 cm×3 cm (2) Weight (75 g/1 m$_2$)×(0.15 m×0.15 m×4 pcs)=75×0.09 m$^2$ Experimental Example 2

In the present experimental example, in case where an apparatus for producing air containing minus air ion according to the present invention is installed and not installed in an office within a building, how different phenomena occur are compared.

(1) Apparatus used

The construction is different from that used in Experimental Example 1 in the following:

1) The size of the effective plane of the vent contract portion using the electric stone carrying rayon in Experimental Example 1 is 15 cm×15 cm, whereas the size thereof in the present example is 25 cm×25 cm, which is about twice of the former. In each case, four non-woven fabrics are placed one above another.

2) Standards of a vent (exhaust) fan used in Experimental Example 2: axial flow type, 12 VDC; rated input, 1.2w; maximum air quantity, 0.33m$^2$ (Made by Shiko Giken Co., Ltd., 0610 type)

Rooms where this apparatus is installed and not installed: size, 12 Tsubo; location, 8 fl., reinforced concrete building 9-story building (20 years after built) located at 1-chome, Ginza, Chuo-ku, Tokyo.

I Room A (one unit of the present apparatus is installed.)

The apparatus was continuously operated. The results obtained one month (30 days) after use were noted. Room B is a conference room, where the apparatus was used for one day (a few times). No person is normally present.

1) Number of person stayed: men–4, women–1

Smokers: 2 men; others, nonsmokers

With respect to smell within the room, evaluation common to all the persons was gathered.

Before the apparatus is installed, persons always felt uneasy about smell of cigarettes. Particularly when they entered the room in the morning, they felt the smell most. When about 3 days passed after the apparatus was installed, no smell of cigarettes was felt (according to the opinion of all the persons). Particularly when they entered the room in the morning, they felt it clearly. On day after holiday, not only the smell of cigarettes has gone but also pleasant air was felt. Not only persons who always stayed in the room but also those who happen to come in the room have the same evaluation.

2) Walls of the room were newly painted 10 days before the apparatus is installed. They felt uneasy about the smell of painting. This smell after the apparatus was installed lasted longer than the smell of cigarettes, about one month being taken.

3) Room B where no apparatus is installed is a conference room. Therefore, the staying hour of persons using this room is about ⅓ of the room A in total hours. The smell of cigarettes was clearly felt by all the persons. Particularly when entering the room, the smell was strongly felt. The smell of paint somewhat disappeared after one month but not completely disappeared.

Evaluations:

1. Deodorizing effect for the smell of cigarettes is remarkable. Particularly, there is no remaining odor due to adhesion to walls, floors, clothes, etc.

2. Effect for chemical coating is not particularly remarkable but can be obtained.

Figure 2:
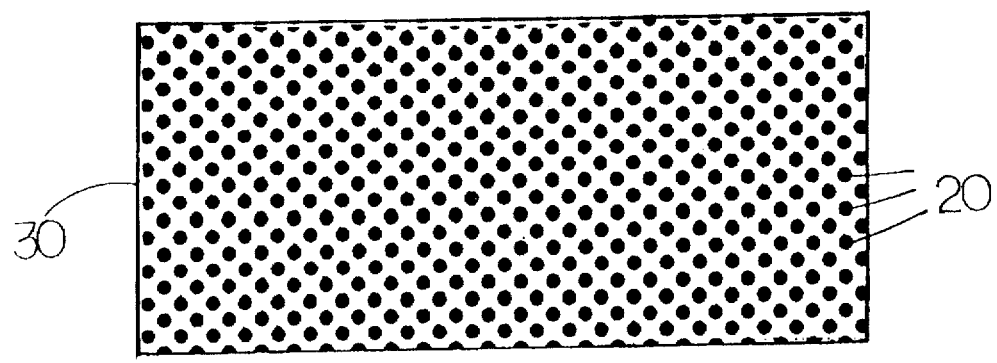
FIG. 2 is a fragmentary view of a plane in an enlarged scale of a vent contact reaction portion used in the apparatus for an apparatus for producing air containing minus alkali ion according to the present invention.

The apparatus and method for producing air containing minus alkali ion according to the present invention will be described in detail by way of specific embodiments referring to the accompanying drawings. First, with respect to the apparatus, there is an electric stone fine powder 20 as shown a plane enlarged fragmentary view of FIG. 2. The electric stone fine powder 20 has the grain size of 0.3 to 3 microns on the average. Next, there is an electric stone carrier 30. The electric stone carrier 30 has the electric stone fine powder 20 uniformed mixed therewith, which is a cloth-like configuration having a volume intrinsic DC electric resistance of $10^{10}$Ωcm.

Figure 3:
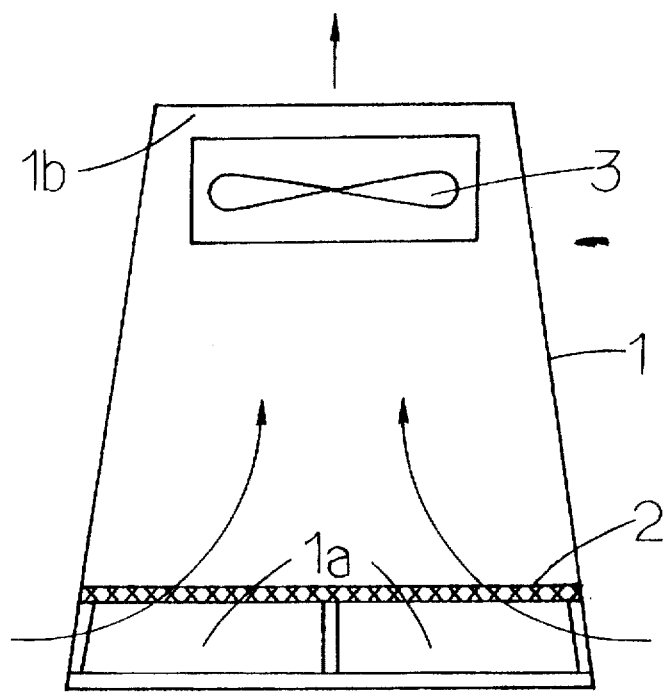
FIG. 3 is a front sectional view of one embodiment of the apparatus for an apparatus for producing air containing minus alkali ion according to the present invention.

Of course, the electric stone carrier 30 has the properties as a carrier, and may be any kind which has a large air contact area such as a honeycomb-like article or a granular article. From the foregoing, a vent contact reaction portion 2 is constituted as shown in a front sectional view of FIG. 3. This portion is located above an air intake 1a at the bottom of the box 1 to cover the whole surface of an air passage of the box 1. There is provided ventilation means 3 formed from an electric fan. The ventilation means 3 causes the vent contact reaction portion 2 constituted by the electric stone carrier 30 containing the electric stone fine powder 20 to subject to the direct forced ventilation into contact with air whereby a minus alkali ion is prepared from water molecules which are moisture in air. The air containing the minus alkali ion is fed out of the air port 1b provided at the upper part of the box 1 to the installation location. In the case where this is applied to a sauna bath, since a natural convection making use of a difference in temperature between upper and lower portions of the sauna bath can be utilized, the above-described ventilation means 3 is not necessary.

Alternatively, water in contact with the electric stone carrier 30 may be provided so that the water comes in contact with the whole or a part of the electric stone carrier 30. That is, the whole or a part thereof is immersed into a watercontained vessel, and the surface of water comes in contact with air by the ventilation means whereby ion molecules of a monomolecular film of hydroxyl ion oriented on the surface of water are evaporated from the water surface along with the water molecules to produce air containing hydroxyl ion. Alternatively, the electric stone carrier 30 may take the construction that he electric stone carrier 30 itself is a vessel, and water is injected into the vessel, the vessel is subjected to forced ventilation through the surface of water to come in contact with air. Further, in the case where this is applied to a sauna bath, since a natural convection within the sauna bath can be utilized, the above-described ventilation means 3 is not necessary.

An embodiment of the method for producing air containing minus alkali ion according to the present invention will be described below. Electric stone fine powder 20 having the grain size of 0.3 to 3 microns on the average is uniformed mixed, which has a volume intrinsic DC electric resistance of $10^7$ to $10^{10} \Omega.cm$, and is brought into contact with the electric stone carrier 30 having a large air contact area having a cloth-like, honeycomb-like or granular configuration through direct forced ventilation by ventilation means 3 formed from an electric fan 3 whereby water (moisture) in air is ionized to prepare hydroxyl ion corresponding to minus air ion. As described above, alternatively, water in contact with the electric stone carrier 30 may be provided so that the water comes in contact with the whole or a part of the electric stone carrier 30.

The following conditions are preferable for embodying the apparatus and method for producing air containing minus alkali ion.

1. The presence of water molecules as moisture components in air is an important element. Accordingly, the apparatus and method for producing minus air ion can be combined with all kinds of moistening methods and apparatuses (a supersonic spray system, an evaporation system, and a system in which water is immersed into a water absorptive material for evaporation) to provide the adequate using conditions as follows:

2. A generally pleasant humidity is said to be 40% to 60% at a relative temperature and a minus ion is contained to enlarge the range of the humidity, which is therefore excellent. A humidity recorder provided so that the humidity is manually or automatically adjusted to keep the humidity within that range.

3. When the humidity exceeds 60%, it is desirable that the humidity is removed but a cooling device normally achieves this object.

(Note) In the air containing hydroxyl ion, the ion is adsorbed and absorbed into water in the surface of the body or underclothes so that the evaporation of water increases to lose the evaporation heat, and one feels that the humidity is lower than normal humidity. Even in a summer season, one feels refreshed.

Figure 4:
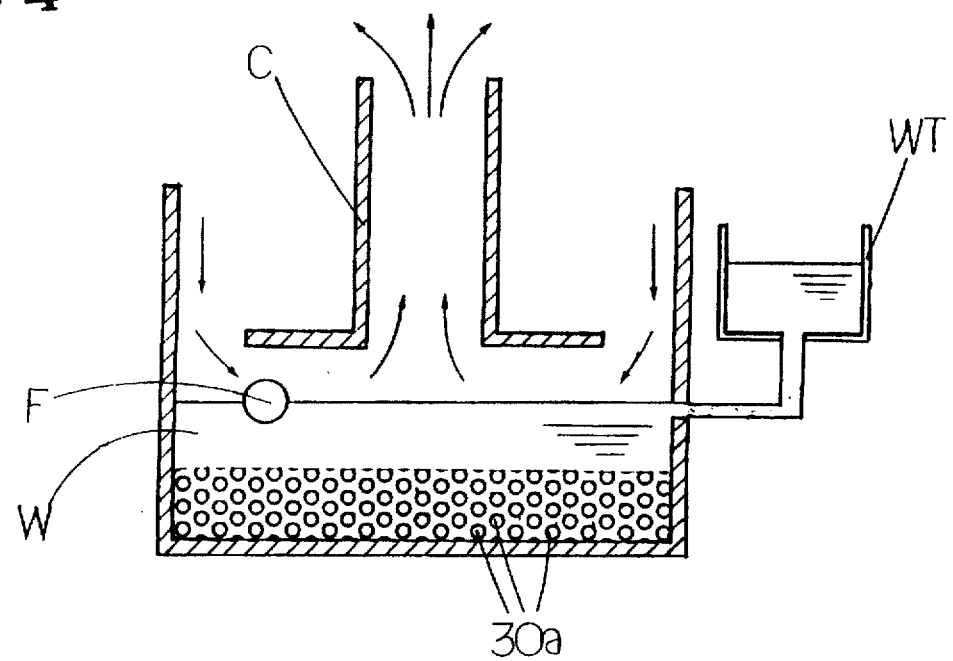
FIG. 4 is a front sectional view of one embodiment in which the apparatus for an apparatus for producing air containing minus alkali ion according to the present invention is applied to a sauna.

In the following, claims 1 and 2 are put in order. Both claims 1 and 2 are the same in that a fan is used for ventilation but are different in that in claim 1, the carrier 30 is brought into contact with the assembly of water molecules as moisture components in air to utilize a discharge by way of boundary release of electrons. On the other hand, in claim 2, by use of means for dipping the carrier into water in the vessel, hydroxyl ion is continuously generated in advance by the feeble electrolysis due to contact between the carrier 30 and water as a liquid to form a monomolecular film with the hydroxyl ion oriented on the surface of water, whereby water in which hydroxyl ion is saturated is evaporated from water on the surface which tends to be evaporated by venting by which the surface of water is prepared by a method as shown in FIG. 4 to form air corresponding to minus air ion containing the ion in air. In the figure, WT is a water tank, 30a designates an electric stone carrier containing electric stone fine powder of ceramic granular material, F designates a water level adjusting float, C designates a relapse opening of a smoke-stack effect for releasing hydroxyl ion, and W designates water.

Claim 2 is greatly different from claim 1 in that in claim 2, use is made of electrolysis at a feeble decomposition pressure or less by way of water as a liquid and a permanent electrode of electric stone fine powder 20, and in claim 1, use is made of a discharge function between an assembly of water molecules in air (moisture component) instead of water as a liquid and a permanent electrode of the electric stone fine powder 20. In claim 2, if the electric stone carrier 30 and water as a liquid and a vessel in which they comes in contact are used, the ventilation method may be of a fan or a smoke-stack effect (which makes use o a difference in temperature between upper and lower portions of vent). One in claim 1 is cheap as general goods and easily handled in views of the construction and operation of the apparatus and necessary energy. However, an attempt is made to rapidly provide a new sauna goods in which "air" in "sauna" presently widely used in the world is changed into air containing hydroxyl ion and an effect of minus alkali air ion in addition to the present sauna effect is added to the sauna. Thus, claim 2 is added.

However, actually, the rayon carrier and a rubber carrier cannot be used in the sauna in terms of heat resistance. In this respect, the ceramic carrier is optimal in all respects. The smoke-stack effect using a heat convection will suffice, and use of a fan in the sauna is difficult. In consideration of the present situation as described above, the following is reviewed. These are also filed this time. Claim 2 is a separate application in which a sauna portion is divided later, and particularly its embodiment is mentioned in a sauna. A difference is clear because no discharge nor rayon is used and there is no ventilation by way of a fan.

In this way, air taken-in from the lower part of the box 1 evenly passes through the vent contact reaction portion 2. Ventilation means 3 formed from an electric fan is provided. In the ventilation means 3, the vent contact reaction portion 2 constituted by the electric stone carrier 30 containing the electric stone fine powder 20 is subjected to direct forced ventilation to contact with the air. Hydroxyl ion which is a minus alkali ion is prepared by the discharge reaction between water molecules as moisture component in the air and the permanent electrode of the electric stone fine powder 20, and the hydroxyl ion which is the minus alkali ion are delivered out of the air opening 1a provided at the upper part of the box I into a space.

As described above, in the case where the minus alkali ion bath is used along with the high temperature air bath of sauna applied to the sauna bath, a flow of air due to the natural convection provided by making used of a difference in temperature between upper and lower portions of air within the sauna bath can be brought into contact with the electric stone carrier, and therefore, it is considered that the ventilation means 3 is unnecessary.

In this manner, by immersing the electric stone carrier, for example, ceramic pellets, into the vessel containing water therein, water molecules are ionized into hydrogen ion $H^+$ and $OH^-$ ion by the electrolytic reaction produced between the fine permanent electrode of the pellet in water. $H^+$ is formed into $H_2$ (hydrogen gas) and liberated from water, and the remaining OH– ion is bonded with water molecules to provide a hydroxy ion $H_3O_{2-}$. This molecule is an anion surfactant molecule, which comprises H–O as a hydrophobic group and $H_2O$ naturally as a hydrophilic group, being charged with a minus charge as a molecule.

Figure 5:
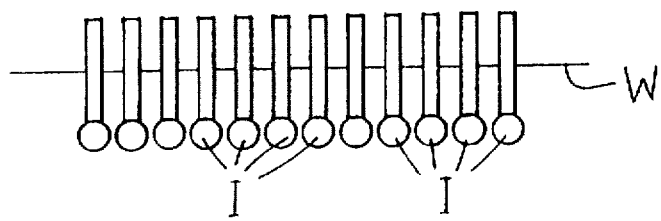
FIG. 5 is an explanatory view of an enlarged portion in the state where monomolecular films are formed on the surface of water.

Since the presence of the molecule bonded with the hydrophobic group is unstable, it is rapidly oriented with the boundary (wall surface) between the surface of water and the solid with the hydrophobic group directed in the direction opposite to water to prepare a monomolecular film. After the boundary has been covered with the monomolecular film, the hydroxyl ion is hard to be dissolved into water whereby the speed of reaction to prepare the ion rapidly reduces. That is, the concentration of hydroxyl ion I with respect to water due to the aforesaid reaction is saturated. In this way, as shown in FIG. 5, a monomolecular film is formed on the surface of water W. The bonding force between water molecules becomes weakened and as a result, the evaporation of water W from the surface is quickened. This brings forth a rise in humidity of a closed space, and the humidity thereof rises.

On the other hand, the flow of air in contact with the surface of wager formed compulsorily or due to the convection absorbs, in air, water which tends to evaporate due to the presence of hydroxy ion, and as a result, air is formed into air containing hydroxyl ion. Thereby, the saturated state of the ion which disappears from the surface of water disappears, and the electrolytic reaction between the water and the electrode of the electric stone again starts to replenish hydroxyl ion. The foregoing is the order of continuously supplying hydroxyl ion to an air current in contact with the surface of water merely by dipping the electric stone carrier into water. However, a supply of water is necessary, which is controlled by making the depth of water level constant.

Being the apparatus and method for producing air containing minus alkali ion according to the present invention configured as described above, there brings forth many effects as follows. That is, with this, the air containing hydroxyl ion which is minus alkali ion is released to a space such as indoor to thereby promote the health of human body as described above.

Further, deodorizing and cleaning effect are brought forth as described below. That is, the air containing hydroxyl ion produced according to the present invention is continuously circulated into a predetermined space whereby rank odors within the space is extinguished and fresh air can be produced. The odor of cigarettes is roughly divided into two, one being volatized as gas during burning, and the other being such that fine particles of oil substances such as nicotine floats in air in the state of fume and the rank odor components are volatized from the surface of the particles. Out of these two odors, the latter slowly floats in air as particles, and adheres to clothes and furnitures, and after adhesion, the rank odors keeps to be generated by volatile components for a long period of time.

Figure 6:
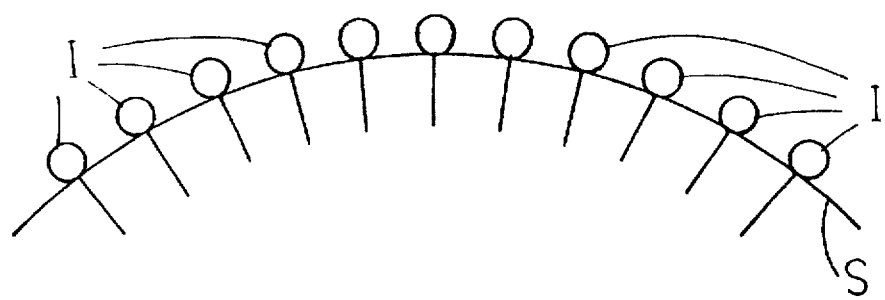
FIG. 6 is an explanatory view of an enlarged portion of monomolecular films to prepare surfactant substance hydroxyl ions oriented on the surface of oily substance.

That is, as shown in FIG. 6, the fume S of cigarettes is an oily substance. Accordingly, the surface of the oily substance is bonded with a hydrophobic group of the surfactant substance. As a result, this surface is covered with water molecules of a hydrophilic group. Therefore, the surface of the oily fine particles is apparently covered with water. Thus, the coagulation of particles with each other and the adhesion thereof to the solid such as walls are lost, and they float in air and move out of the room riding on a current stream of vent or exhaust. Accordingly, the oily particles which cause to produce the odor of cigarettes disappear. That is, instead of the expression, the deodorizing of fumes of cigarettes, it is suitable to use the expression that the oily substance of the fumes of cigarettes constituting the rank odor substance is embraced by the hydroxyl ion I and sent out. FIG. 6 is an explanatory view of a monomolecular film formed by the surfactant substance hydroxyl ion. It is understood to be directed in the direction opposite to the orientation of the monomolecular film in the surface of water described above.

In this manner, the hydrophobic group of the hydroxyl ion is bonded with the surface of the particles to embrace it, and the surface of the oily fine particles (charged with plus) is apparently covered with the monomolecular film of water thereby providing fine particles free from adhesion. The fine particles free from adhesion can be easily discharged outside the room by ventilation without staying within the room.

Figure 7:
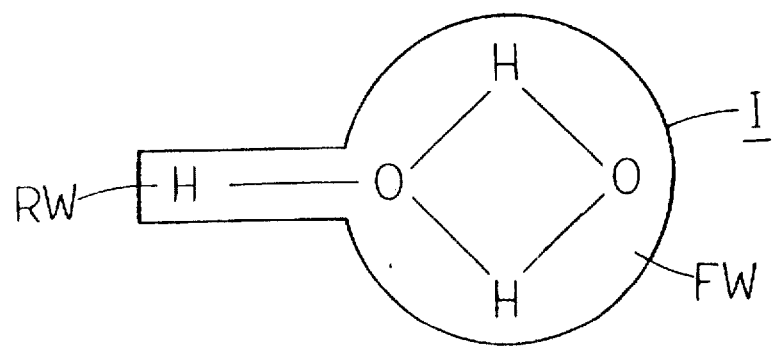
FIG. 7 is an enlarged explanatory view of a hydroxyl ion.

With respect to the removal of those other than the odor of cigarettes, there is no remarkable effect of removal for the odor of coating such as walls. The effect of removal of body odors in a closet which is easily filled with a body odor, a wardrobe, a dressing room, a locker room and the like is remarkable. The air in the room containing hydroxyl ion not only causes the rank odor of cigarettes or the like to disappear but also air feels to be refresh. The reason why is a problem to be solved in future. As described above, there exists a great effect of creating air having a refreshing for removal of rank odors in the space in addition to the effects for health and medical treatment of human being. FIG. 7 is an enlarged explanatory view of hydroxyl ion I. In FIG. 7, RW indicates a hydrophobic group (charged with minus), and FW indicates a hydrophilic group ($H_2O$).

What is claimed is:

1. An apparatus for producing air containing minus alkali ions, comprising an electric stone fine powder having a grain size of 0.3 micron to 3 micron on the average, an electric stone carrier having said electric stone fine powder uniformly mixed therewith whose volume intrinsic DC electric resistance is $10^7$ to $10^{10}$ $\Omega$.cm and having an area in contact with air, and ventilation means for subjecting said electric stone carrier to direct forced ventilation to contact air.

2. The apparatus for producing air containing minus alkali ions according to claim 1, wherein the electric stone carrier comprises a fiber, a rubber elastic substance or a ceramic.

3. An apparatus for producing air containing minus alkali ions, comprising an electric stone fine powder having a grain size of 0.3 micron to 3 micron on the average, an electric stone carrier having said electric stone fine powder uniformly mixed therewith whose volume intrinsic DC electric resistance is $10^7$ to $10^{10}$ $\Omega$.cm, a whole or a part of said electric stone carrier being in contact with water, and ventilation means for subjecting the surface of said water to forced ventilation to contact air.

4. The apparatus for producing air containing minus alkali ions according to claim 3, wherein the electric stone carrier comprises a fiber, a rubber elastic substance or a ceramic.

5. A method for producing air containing a minus alkali ion, comprising:
   subjecting an electric stone carrier having an electric stone fine powder having a grain size of 0.3 micron to 3 micron on the average uniformly mixed therewith, said carrier having a volume intrinsic DC electric resistance of $10^7$ to $10^{10}$ $\Omega$.cm and having an area in contact with air, to direct forced ventilation by ventilation means to contact air, and
   ionizing water in the air to produce a minus alkali ion.

6. The method for producing air containing a minus alkali ion according to claim 5, wherein the electric stone carrier comprises a fiber, a rubber elastic substance or a ceramic.

7. A method for producing air containing a minus alkali ion, comprising:
   subjecting a surface of water in contact with a whole of a part of an electric stone carrier having an electric stone fine powder having the grain size of 0.3 micron to 3 micron on the average uniformly mixed therewith, said carrier having a volume intrinsic DC electric resistance of $10^7$ to $10^{10}$ $\Omega$.cm, to forced ventilation by ventilation means to contact air, and ionizing water in the air to produce a minus alkali ion.

8. The method for producing air containing a minus alkali ion according to claim 7, wherein the electric stone carrier comprises a fiber, a rubber elastic substance or a ceramic.

* * * * *